US009868651B2

(12) United States Patent
Matlack et al.

(10) Patent No.: US 9,868,651 B2
(45) Date of Patent: Jan. 16, 2018

(54) SOLAR DISINFECTION OF FLUID

(71) Applicant: PotaVida, Inc., Seattle, WA (US)

(72) Inventors: Charles Bruce Matlack, Seattle, WA (US); Tyler Blake Davis, Seattle, WA (US); Jacqueline Callihan Linnes, West Lafayette, IN (US)

(73) Assignee: PotaVida, Inc., Seattle, WA (US)

( * ) Notice: Subject to any disclaimer, the term of this patent is extended or adjusted under 35 U.S.C. 154(b) by 0 days.

(21) Appl. No.: 14/983,267

(22) Filed: Dec. 29, 2015

(65) Prior Publication Data

US 2016/0251238 A1    Sep. 1, 2016

Related U.S. Application Data

(60) Provisional application No. 62/120,982, filed on Feb. 26, 2015.

(51) Int. Cl.
*C02F 1/32* (2006.01)
*C02F 1/00* (2006.01)
(Continued)

(52) U.S. Cl.
CPC .............. *C02F 1/325* (2013.01); *C02F 1/008* (2013.01); *C02F 1/02* (2013.01); *G01J 1/0271* (2013.01); *G01J 1/429* (2013.01); *C02F 2201/009* (2013.01); *C02F 2201/3228* (2013.01); *C02F 2209/02* (2013.01); *C02F 2209/11* (2013.01);
(Continued)

(58) Field of Classification Search
CPC .... C02F 1/008; C02F 1/02; C02F 1/30; C02F 1/32; C02F 1/325; C02F 2201/009; C02F 2201/3228; C02F 2209/02; C02F 2209/11; C02F 2209/44; C02F 2303/04; G01J 1/0271; G01J 1/429
See application file for complete search history.

(56) References Cited

U.S. PATENT DOCUMENTS 7,514,006 B1 *  4/2009  Lundquist ............... C02F 1/002
                                                         210/407
2009/0284732 A1 * 11/2009  Vitale ................... B65D 23/16
                                                          356/51

(Continued)

FOREIGN PATENT DOCUMENTS

ES     EP 2835622 A1 *  2/2015  ............. G01J 1/429
WO     WO 2013033144 A2 *  3/2013  ............. C02F 1/325

*Primary Examiner* — Mark R Gaworecki
(74) *Attorney, Agent, or Firm* — Lane Powell PC

(57) ABSTRACT

A system for solar disinfection of fluid. One most preferred version of the system includes:
 (a) A UVTC, made of a polyethylene laminate film with an approximately rectangular plan, providing:
  a. A first compartment.
  b. A second compartment for holding fluid, with a port to fill and dispense.
 (b) A Disinfection Monitor Module ("DMM") located in the first compartment which:
  a. Includes at least one sensor to measure radiation intensity.
  b. Provides at least one user interface:
  c. Contains a wireless communication interface.
  d. Operates according to a process that ensures sufficient cumulative exposure of the contained fluid to solar UV to achieve adequate solar disinfection.
Alternative embodiments may also include sensors to detect additional characteristics, such as transmittance, turbidity, "combined transmittance," and/or temperature.

19 Claims, 9 Drawing Sheets

(51) Int. Cl.
*G01J 1/42* (2006.01)
*C02F 1/02* (2006.01)
*G01J 1/02* (2006.01)

(52) U.S. Cl.
CPC ...... *C02F 2209/44* (2013.01); *C02F 2303/04* (2013.01)

(56) References Cited

U.S. PATENT DOCUMENTS

| | | | | |
|---|---|---|---|---|
| 2010/0025339 | A1* | 2/2010 | Lundquist | C02F 1/002 210/749 |
| 2010/0314306 | A1* | 12/2010 | Wadstrom | C02F 1/30 210/175 |
| 2011/0215054 | A1* | 9/2011 | Lantis | B65D 51/00 210/748.1 |
| 2012/0118803 | A1* | 5/2012 | Sodankur | C02F 1/14 210/175 |
| 2012/0318997 | A1* | 12/2012 | Wesian | C02F 1/32 250/373 |
| 2013/0020500 | A1* | 1/2013 | McKinney | A61L 2/10 250/436 |
| 2014/0170399 | A1* | 6/2014 | Bhattacharya | B32B 27/08 428/216 |
| 2014/0341777 | A1* | 11/2014 | Deshays | A61L 2/24 422/24 |
| 2015/0021243 | A1* | 1/2015 | Herrington | C02F 1/002 210/85 |
| 2015/0307368 | A1* | 10/2015 | Yanke | C02F 1/325 210/660 |

* cited by examiner

SOLAR DISINFECTION OF FLUID

CROSS REFERENCE TO RELATED APPLICATIONS

This patent application claims the benefit of and priority to U.S. Provisional Patent Application Ser. No. 62/120,982 filed on Feb. 26, 2015, entitled "System And Method For Solar Disinfection Of Fluid," the disclosure of which is hereby incorporated by reference for all purposes.

TECHNICAL FIELD

The disclosed subject matter pertains generally to solar disinfection ("SODIS"), and more particularly, to a self-contained, portable disinfection unit.

BACKGROUND INFORMATION

Ultraviolet ("UV") light can be used as a means for disinfection. In particular, UV light from the sun can be used to disinfect fluids such as water. The intensity of UV light, exposure time, temperature, and cloudiness of the water are important variables to determine the rate of disinfection. SODIS is a procedure to disinfect contaminated fluid, typically drinking water, using solar radiation. Very generally stated, contaminated fluid is poured into a transparent container and exposed to the sun. Solar radiation, particularly UV radiation approximately in the wavelengths of 320-400 nm (UV-A and UV-B), inactivates pathogens (e.g. bacteria, viruses, and other microorganisms) in the fluid; in the case of water, rendering the water safe for human consumption. The solar radiation also heats the contaminated water, and temperatures above 40 degrees Celsius (C) enhance this process. Further, if the water is maintained above a certain temperature for a sufficient period of time, e.g. 60 degrees C. for 1 hour, the heat kills pathogens and renders the water safe for human consumption (solar pasteurization). Studies have shown that the process by which solar radiation eliminates pathogens is accelerated when the water is at higher temperatures. The presence of certain chemicals and compounds, such as photocatalysts (typically titanium oxide), photosensitizers, and dissolved oxygen in the water will also accelerate the SODIS process.

SODIS is advantageous over other forms of disinfection for a number of reasons. Principally, the process is more economical than boiling or chemically treating contaminated water. In many areas lacking adequate access to potable water, fuel for boiling can be quite expensive and chemicals for treating water prohibitively so, if available at all. SODIS, by contrast, only requires an ultraviolet transparent container ("UVTC") and readily-available solar radiation, preferably strong sunlight. Additionally, SODIS is more environmentally friendly than other disinfection methods. Because the process uses only renewable solar energy, water can be disinfected without the use of fuel and without requiring any consumable media, such as chemicals or replacement filter media. Approximately five million people currently practice SODIS using polyethylene tetraphthalate (PET) beverage bottles.

Challenges With SODIS

Even though SODIS is conceptually simple, there are several practical challenges. These challenges generally reduce to knowing whether, when, and to what degree the process is underway and complete. Proper SODIS requires the right container, level of fluid cloudiness, and strength of solar radiation, which is a function of location and weather. Further, when faced with non-ideal conditions, such as cloud cover or weak sunlight, SODIS requires extended solar exposure and/or recognizing that SODIS is infeasible with a given set of conditions. Some factors, such as solar UV intensity, are unobservable with the naked eye. Further, it is impractical to manually measure and adjust for time-varying factors related to weather.

Given the practical challenges of SODIS, a set of general guidelines have been developed to increase the likelihood of conducting it correctly. It is typically recommended that water be exposed to direct sunlight for six (6) to eight (8) hours in good conditions, which include relatively clear water (<30 NTU, Nephelometric Turbidity Units), minimal cloud cover, and proximity to the equator. Contaminated water left outside for eight (8) hours during a period of moderate cloud cover may have received only a fraction of the radiation necessary to ensure disinfection. Thus, a person consuming the water could still become sick due to pathogens. In contrast, the disinfection process may move more quickly at high altitudes or nearer the equator where solar radiation doses tend to be higher, so that water may be disinfected more quickly than the time recommended by general guidelines.

In short, varying environmental and water quality factors can create uncertainty as to whether and to what degree the water has been adequately disinfected by solar radiation. This uncertainty prevents widespread use of an otherwise economical and environmentally-friendly method of treating contaminated drinking water. Thus, a system and method that correctly determines and indicates when the SODIS process is underway, to what degree SOIDS has progressed and whether it has completed, under a given set of conditions would greatly improve the dependability and consequently utility of the SODIS process. This would promote greater use of the SODIS process and allow for increased access to potable water.

SUMMARY OF THE INVENTION

Generally stated, the invention is directed to a solar disinfection system. Embodiments include a system and method for determining when SODIS is underway and to what degree SODIS is complete within a volume of fluid. Embodiments implement a container having a first compartment for containing fluid and a second compartment for housing a Disinfection Monitor Module ("DMM"). The container is configured such that in operation the container defines a first surface substantially normal to a direction of radiation, and the container orients a sensor portion of the DMM such that it is also substantially normal to the direction of radiation.

Various embodiments implement one or more additional sensors for enhancing the performance of the system, such as a temperature sensor. Still other embodiments implement one or more additional emitters, such as optical emitters or RF emitters for communicating data external to the system.

DETAILED DESCRIPTION OF EMBODIMENTS

Figure 1:
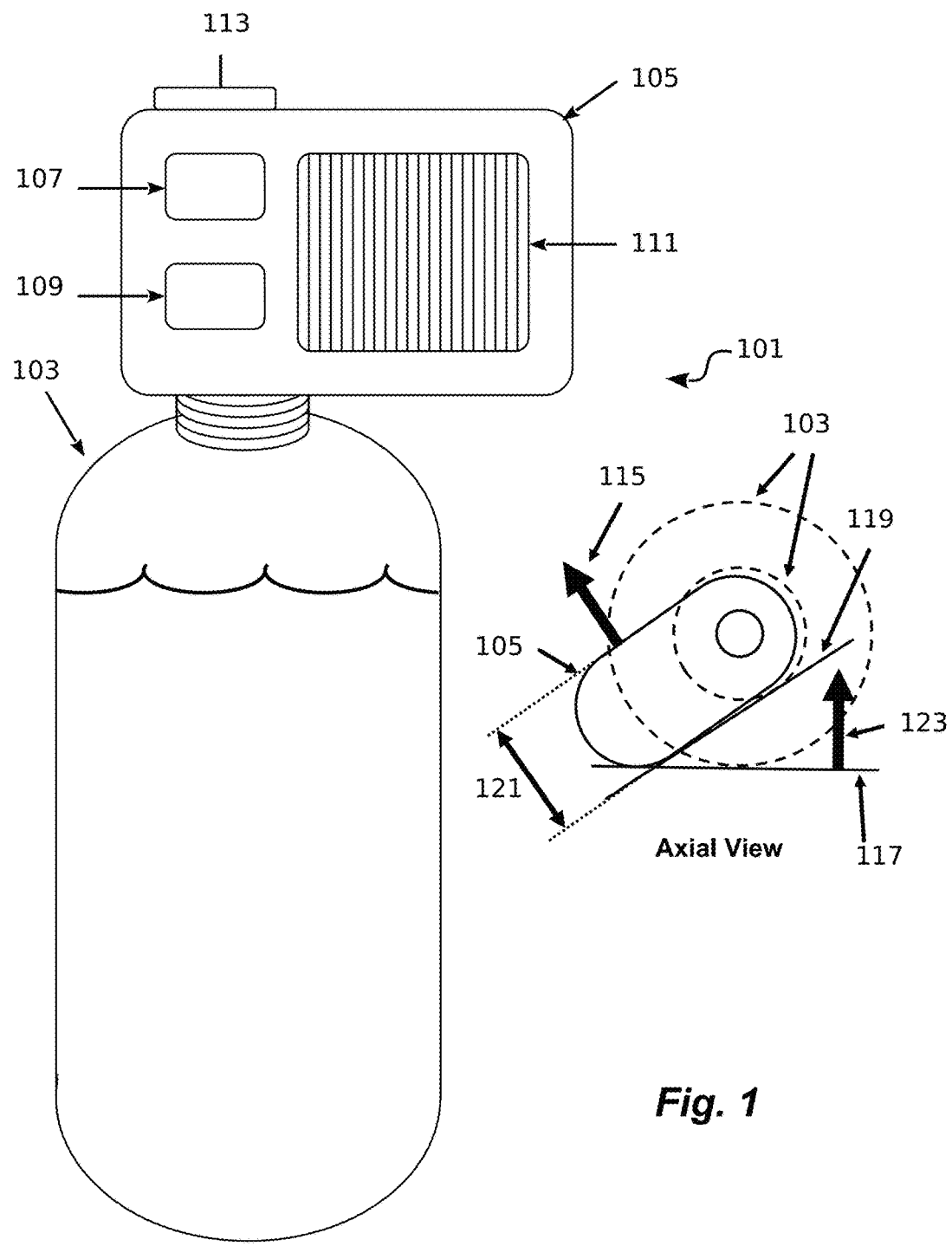
FIG. 1 is a shows a typical SODIS device.

Generally described, embodiments provide a solar disinfection system that measures factors, including at least UV intensity. One core system includes a UVTC and an attached Disinfection Monitor Module ("DMM"), wherein the DMM measures and/or estimates the UV intensity received by the fluid within the UVTC. By way of outline, this disclosure will begin with a brief glossary of terms, followed by a discussion of certain advantages that the disclosed embodiments have over other SODIS designs. Finally, the disclosure will proceed with a detailed discussion of those disclosed embodiments.

Glossary of Terms

As used throughout this document, the following terms have the following meanings unless otherwise specified:

"Solar Disinfection" (SODIS): A process of exposing contaminated water to sunlight, particularly the ultraviolet (UV) components, sufficiently to render harmless pathogens (bacteria, viruses, cysts, and other microorganisms capable of causing sickness if ingested). SODIS is mediated by UV light interacting with molecules within the water and pathogens to cause several types of chemical reactions.

"Solar Pasteurization": A process of exposing contaminated water to sunlight in order to heat it sufficiently to kill any pathogens via pasteurization, typically requiring a temperature at or above approximately 60 C for approximately 1 hour.

"Disinfection Monitor Module" (DMM): A system for measuring solar disinfection.

"UV Transparent Container" (UVTC): A container which allows ultraviolet (UV) solar energy from the sun to pass through its surface and to a contaminated fluid within.

"Fluid": A fluid, typically liquid water, which contains impurities, including viable pathogens, and requires disinfection in order to be potable.

"Light": Optical-wavelength radiation, including but not limited to ultraviolet radiation from the sun.

"Transmittance": The proportion of light passing unimpeded through a section of fluid or other material.

"Turbidity": The ratio of light scattered at 90 degrees to the light transmitted through a small fluid sample volume.

"Combined transmittance": The proportion of light generated by an emitter that is detected by a sensor some distance away and oriented towards the emitter.

Combined transmittance may differ from transmittance in that the light may take multiple indirect paths from the emitter to the sensor.

"Cut and weld": A process for manufacturing plastic bags from one or more layers of film laminate stock, in which the stock is first die-cut into the correct shape, then positioned in a tool which applies pressure and heat (through conduction, ultrasound, radio-frequency, or the like), forming welds between the separate layers. The process can also weld flexible or rigid plastic components to and/or between the stock layers, including handles and fixtures with threaded openings.

Discoveries of the Inventors

The inventors have closely analyzed the SODIS techniques and literature available and envisioned today, and have identified several advantages of the disclosed embodiments over those techniques.

.A Environmental/Water Properties To Measure

Academic literature identifies several factors as important predictors of the solar disinfection process, including UV intensity at different wavelengths, temperature, and cloudiness of the water. Cloudiness can be quantified and measured in different ways, including as light transmittance at specific wavelength(s) through a specific volume of water, and as turbidity. Turbidity is defined (Nephelomteric, ISO 7027) as the intensity of light scattered at 90 degrees to the light transmitted straight through a sample, divided by the intensity of transmitted light. Turbidity is frequently used as a predictor of poor SODIS performance in scientific studies. However, scientific studies have also established that transmittance is in fact a better predictor of SODIS, because it is the absorption, not scattering, of light that retards the SODIS process.

Recognizing that the preference is to understand the amount of light that is actually reaching points within the volume of water, disclosed is an innovative sensor apparatus that makes a measurement similar to transmittance but which is a better predictor of solar disinfection. This measurement is the relative transmittance between an emitter and a sensor, co-axially oriented towards one another, and separated by some distance. Thus, the light from the emitter reaching the sensor is the sum of the directly transmitted light (transmittance) and the scattered light which happens to also reach the sensor (related to, but not equal to, turbidity). The sum of directly and indirectly transmitted light may be designated as the "combined transmittance." Unlike other systems, the disclosed sensor apparatus uses just one emitter and one sensor, and its measured values provide a better prediction of SODIS.

The preferred embodiment provides a sensor apparatus design to better estimate SODIS progress by measuring the "combined transmittance" of light between two points in the fluid volume without restricting transmission to line-of-sight. This emulates the amount of sunlight penetrating the same depth of water as the emitter-sensor separation in the apparatus, as is described below.

.B Liquid Presence Detection

Ideally, the sensor apparatus should not mistake the absence of water for water with a low level of cloudiness, because this will lead to erroneous estimates of turbidity or combined transmittance. The preferred embodiment uses LEDs and photosensors having epoxy dome lenses with refractive indices which make it possible to differentiate the absence of water (or any fluid with a higher refractive index than air) from the presence of water with any level of cloudiness.

.C Temperature Is Not Critical

Elevated temperatures, particularly above about 40 C, are known to increase the rate of SODIS. Further, uneven heating of a vessel used for SODIS causes thermal convection, which aids the process by exchanging water in greater- and lesser-exposed locations within the volume, mitigating the effects of cloudiness. Uneven heating and circulation make it difficult to predict the SODIS process based on temperature measurement at a single point on the edge of a container, especially when thermal dynamics are easily effected by the temperature and radiated heat absorbance of the surface on which a transparent container is placed. Under no normally encountered temperatures is the SODIS process slower than standard rates which are observed up to about 40 C; therefore, temperature is typically not expected to make SODIS infeasible.

.D Modeling Algorithm

The use of cumulative UV exposure as the predictor for SODIS progress is simpler than other models which incorporate temperature or turbidity, but sufficient and reliable when the turbidity of the water is relatively low (e.g., less than about 30 Nephelometric Turbidity Units (NTU)). Finally, ignoring temperature also prevents false indication of successful disinfection if the fluid next to a temperature sensor is substantially warmer than the temperature of much of the fluid in the UVTC.

To minimize cost while preserving simplicity and robustness to variable conditions, embodiments preferably measure solar UV intensity with a sensor that is selective for wavelengths known to drive SODIS, and in some embodiments measures fluid transmittance over the longest distance possible that does not require substantial mechanical features to accommodate a longer distance.

Advantages Of The Disclosed Embodiments

FIG. 1 depicts a simplified system diagram of one SODIS system that illustrates deficiencies with existing technologies. The SODIS system 101 consists of a transparent bottle 103, a control unit 105, a photosensor 107, a display unit 109, a solar cell 111, and a reset button 113. The control unit 105 is screwed onto the threads of the opening of the transparent bottle 103 and sits at the top of the bottle 103. The photosensor 107, display unit 109, and solar cell 111 are attached to the outer surface of the control unit 105. The system 101 is powered by the solar cell 111 and uses the photosensor 107 to determine the amount of UV radiation the water has been exposed to. Once the system has determined that a sufficient UV dose has been received, the display unit 109 indicates to the user that the water is safe to drink. The system 101 is activated when the user screws the control unit 105 onto the top of the bottle, or when the user presses the reset button 113. The unit also includes a temperature sensor located in contact with the internal volume of the bottle 103.

The inventors have recognized various problems with the typical portable disinfection system shown in FIG. 1, many of which can result in the device erroneously indicating that the water has been disinfected, potentially exposing the user to waterborne pathogens (which could lead to illness).

.A Container

First, the container must be provided by the end-user, which results in a lack of control or accounting for the quality or size of the container. Regarding quality, the container (since it is chosen by the end-user) could be dirty or opaque to UV radiation (e.g. high-density polyethylene) but possibly transparent to visible light (e.g. polycarbonate, or borosilicate glass with impurities). Even a container that normally permits the transmission of UV radiation may deteriorate over time such that it blocks most or all UV radiation. As to size, the container could also be too large, such that some regions of the volume receive too little UV exposure. Existing SODIS users are often impoverished people and they are challenged to produce clean, clear bottles of the recommended material (e.g. PET, polyethylene tetraphthalate). If the bottles used are too small (e.g. 500 mL beverage bottles or smaller), then many are required in order to treat even a modest volume of water.

.B Cloudiness

Second, the SODIS system shown in FIG. 1 cannot control or account for the cloudiness of the water, which can block UV radiation. If the water is particularly cloudy, UV radiation will be absorbed near the surface and fail to reach the deeper water within. This problem is exacerbated if the container is too large, such that the radiation has farther to travel to reach all of the contaminated water.

A user of the system shown in FIG. 1 is required to filter or otherwise clarify the fluid before the SODIS process or risk insufficient disinfection.

.C Sensor Orientation

Third, the location and orientation of an exterior photosensor, as shown in the system of FIG. 1, is not ideal because the photosensor 107 may not receive the same amount of solar radiation as the contents of the bottle 103. As a consequence, the system may either under- or over-estimate solar intensity and thus disinfection rate. Under-estimation occurs if the sensor 107 is pointed away from the sun's path in the sky. In this case, the sensor measures less light than is actually reaching the assembly when the incoming light is not aligned with the orientation (115) of the sensor 107 and control unit 105. Sensor orientation 115 in turn is determined by the surface upon which the user places the control unit and bottle, and by the diameter of the bottle. The sensor has diminished sensitivity to light from directions in which the sensor is not pointed, particularly directions orthogonal to the normal to the surface (123). Still, that light has efficacy on the water in the bottle, but the system 101 will incorrectly record less progress in the SODIS process. In particular, two illustrative examples of the surface orientation with a smaller bottle 119 and with a larger bottle 117 show that unless the housing width 121 of the control unit 105 is equal to the diameter of the largest bottle, the sensor orientation 115 will be substantially skewed from the ideal direction 123 of normal to the surface. In simple terms, unless just the right diameter bottle is used, the sensor 107 will not point straight up, as is preferred, but instead be directed partially sideways and consequently receive less sunlight.

Alternatively, the photosensor 107 and control unit 105 may over-estimate the light reaching the contents of the bottle because light is measured outside the UVTC, and without some other compensatory mechanism for the unknown and variable UV transmittance of the UVTC.

.D User Error

Fourth, to the extent that the system shown in FIG. 1 uses a user-activated reset button (e.g. 113 on FIG. 1), it is susceptible to user error because it depends on manual activation of the system each time a new bottle of contaminated water is used. For example, the control unit 105 could be transferred to a new bottle of contaminated water while it is still processing, so it would falsely indicate that the new water has been adequately irradiated if a manual reset 113 is not activated. Alternatively, the user could fail to activate the system with the reset button 113, e.g. due to confusion about correct usage, and the system would fail to determine how much radiation the water has received.

Accordingly, there is a need for a solar disinfection system that accurately measures the amount of solar radiation that a contaminated fluid has been exposed to even if the fluid is cloudy, without requiring careful placement and orientation of a control unit, and mitigates the risk of incorrect use that could result in sickness.

Discussion Of The Preferred Embodiments

Briefly described, the preferred embodiments are directed to a SODIS system that includes a UVTC and a DMM. In the preferred embodiment, the UVTC and the DMM are arranged in such a way that a rate of disinfection can be measured accurately.

.A General Design

Figure 2:
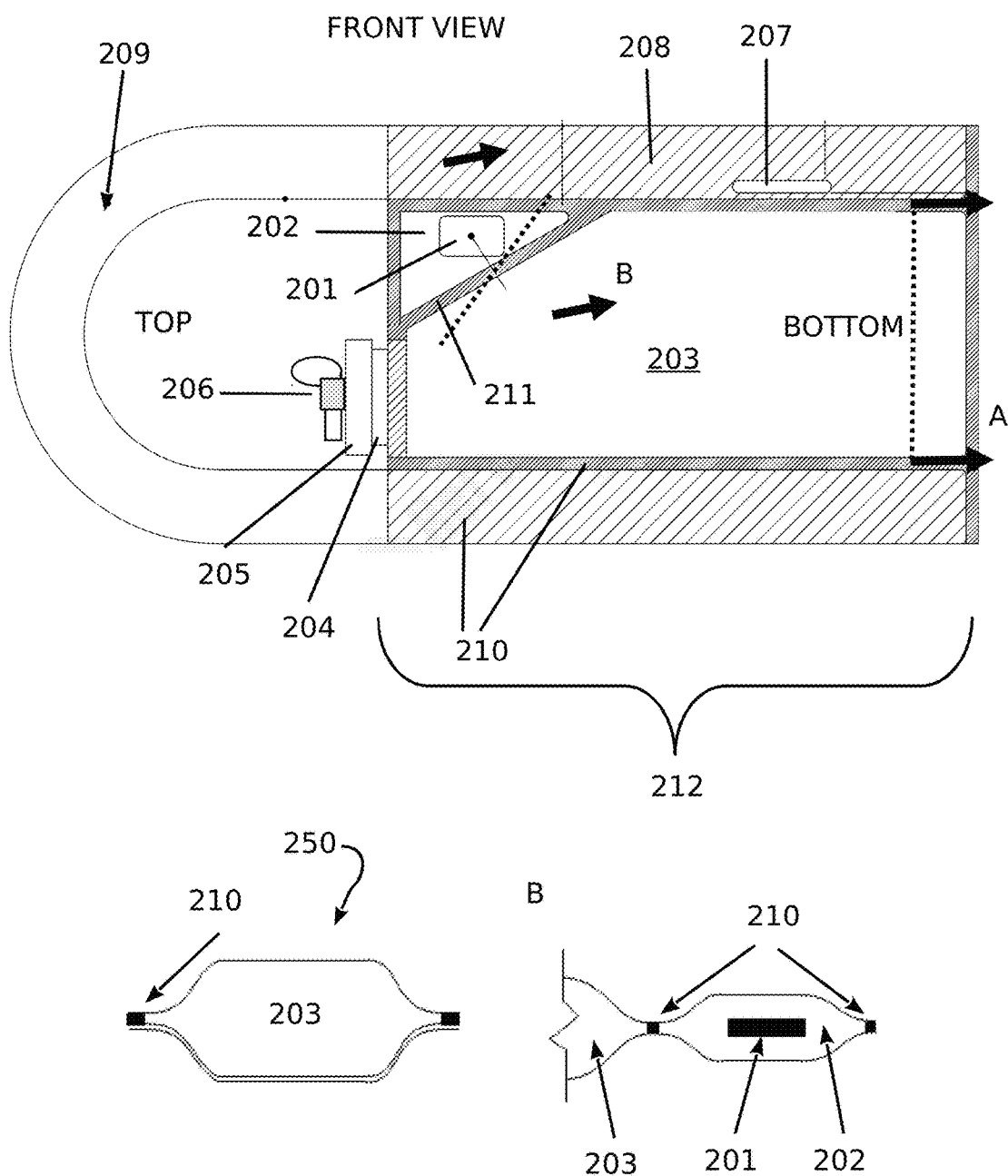
FIG. 2 is an embodiment of the entire novel disinfection system.
Figure 9:
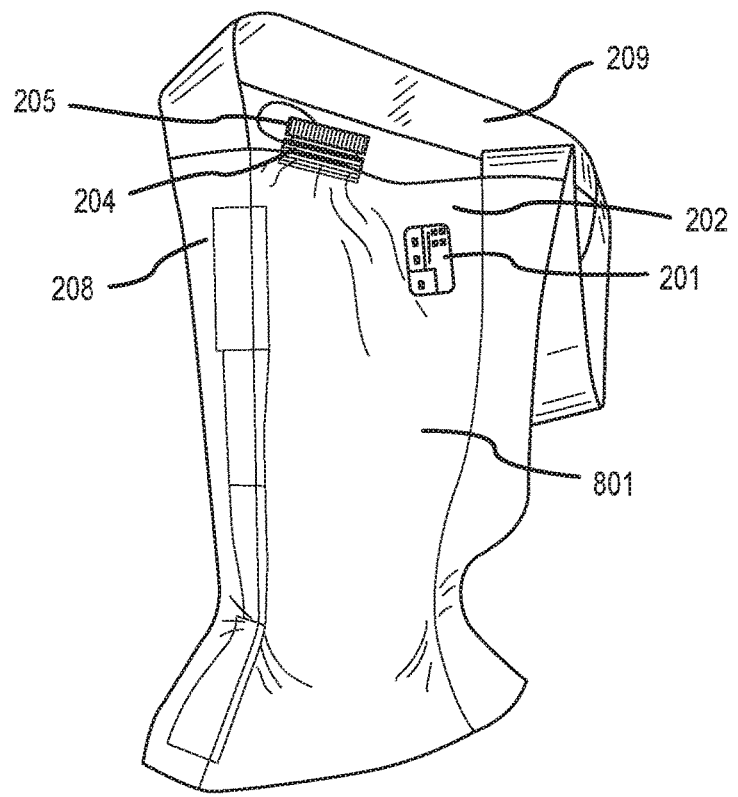
FIG. 9 shows photographs of one embodiment of the preferred system and of one embodiment of the preferred DMM.
Figure 9:
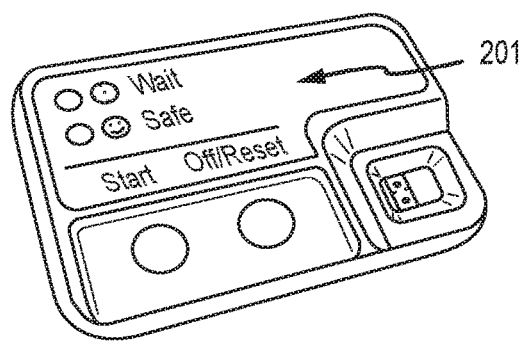

FIG. 2, viewed in conjunction with FIG. 9, shows one embodiment of a disinfection system. The system includes a substantially UV transparent bag (212) with fluid compartment (203) and separate disinfection monitor compartment (202), and includes a fill port (204) at the top of the bag with threaded lid (205) and spigot (206) for dispensing disinfected water. The UVTC of the preferred embodiment is a plastic bag manufactured with a "cut and weld" process. The UVTC preferably includes an integrated DMM (201) encapsulated in the disinfection monitor compartment (202) within the bag (212). Preferably, the disinfection monitor compartment (202) is sealed off from the main compartment (203). The bag (212) of the preferred embodiment holds approximately 10 L of water, and when placed on a substantially flat surface (e.g. the ground) it lies so that the DMM's front face (307 FIG. 3) is oriented upward, normal to the flat surface. This upward orientation of the DMM is partially ensured by a relatively stiff flange (208), possibly incorporating stiffening material in addition to the bag layers, welded around part of the perimeter of the bag (212) and by the rigidity of the encapsulation within compartment 202. The preferred orientation of the DMM allows the UV light sensor to receive as much as possible the same sunlight which also reaches the fluid bag generally.

The DMM (201) and fill port (204) are both located toward the top of the bag (212) to reduce the likelihood that they get dirty or bear the weight of the bag if it is rested against the ground or other surface during use. Further, in case the bag (212) is placed with the spigot (206) overhanging a raised surface—such as may be the case where children can dispense water near head-height—the DMM (201) is in an accessible location for checking disinfection status via the indicators (301, 302 FIG. 3).

The bag material may be a plastic film which has appropriate UV-transmittance at the needed thickness, composed substantially of polyethylene in a laminate with other materials providing mechanical, thermal, and biological properties, including resistance to adhesion of microorganisms. The bag (212) has a generally pillow-like shape when filled, as shown in the cross-sectional view (250). The bag (212) may be assembled using multiple pieces of film joined with welded seams (210) and in addition to transparent film includes reinforced stiffening material (208), made preferably of plastic or the like along some edges. Welding, including thermal, radio-frequency (RF), or ultrasonic methods, is one cost-effective method of joining plastic film laminates for a bag like this.

.B Bag Shape

FIG. 2 shows the unique shape of the preferred embodiment of the UVTC. The preferred embodiment, and others, cause the filled bag to have a cross-sectional depth of less than about about 10 cm, while providing an internal volume near 10 L, and having a shape suggestive of a beverage bottle due to the welded partition creating the compartment for the disinfection monitor. The bag plan of the preferred embodiment is a rectangle with one truncated corner that creates a shape suggesting a large bottle. It can further suggest a jug depending on handle placement at the truncated corner and placement of the fill port.

.C Carry Handles

Two mechanisms for carrying the unit are envisioned: a carry handle (207) comprising a die-cut slot with rounded ends in the reinforced material; or a carry strap (209) composed of the same material but extending beyond the bag edges. Ideally, the unit includes both mechanisms as shown. However, alternative embodiments may include either mechanism or other carry mechanisms not shown. The carry handle (207) allows the unit to be safely carried or suspended, e.g. while dispensing water, with the fingers of one hand inserted in the opening, while the carry strap (209) allows it to be carried hands-free over longer distances by, e.g., wearing the strap over one's shoulder.

.D DMM Construction

Figure 3:
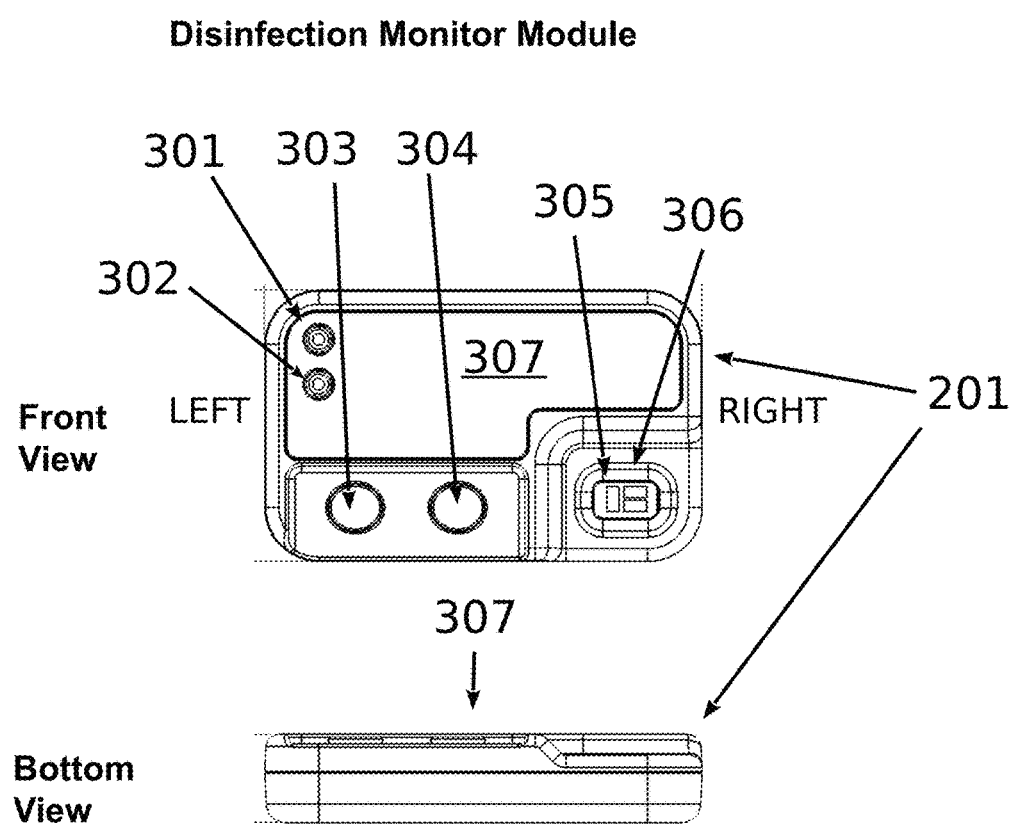
FIG. 3 is a preferred embodiment of the Disinfection Monitor Module ("DMM").

Turning briefly to FIG. 3, shown is an embodiment of the disinfection monitor module (DMM) (201). The preferred DMM is constructed of a 2-piece plastic housing enclosing a printed circuit assembly and two button plungers. Because the DMM (201) is sealed and securely entrapped in its compartment (202), the housing pieces can be preferably joined with snap-lock mechanical features or even friction fit. Many other techniques may be used to join the two pieces, such as RF or ultrasonic welding, with fasteners including screws, or the like. These are but a few examples of the unlimited ways the DMM housing may be constructed.

Five openings are preferably provided in the housing for the buttons (303, 304), visual indicators (301, 302), and light sensor (305) preferably co-located with a wireless emitter interface (306) in a preferably recessed area of the housing to maximize the range of directions from which light can reach both. As illustrated, these openings preferably face directly to the front of the DMM (201). In other embodiments the indicators (301, 302) may be exposed through openings at the corner between the left and front faces of the DMM housing, making them visible from the front side of the bag (212) if the entire system rests on an elevated surface near head-height. Other orientations may also be employed and function equally well.

.E DMM Entrapment Benefits

Returning to FIG. 2, the monitor compartment (202) provides environmental protection for the DMM (201). As a result, the DMM (201) need not be impervious to fluid or dirt, reducing its cost and complexity. The entrapment of the DMM (201) within a compartment (202) of the bag material means that incoming light that reaches the DMM (201) will attenuate at the same rate as incoming light that reaches the fluid within the fluid compartment (203). For this reason, the intensity measured by the sensor (305) is substantially the same as the intensity at the inner surface of the fluid compartment (203). This feature enables the unit to automatically compensate for damage and changes to the transmittance of the bag material over time, ensuring that the UV actually reaching the water is measured, and solving the problem of unknown UVTC properties.

As an alternative to the monitor compartment (202), the DMM may instead be configured for attachment to the bag (212) and a portion of the bag material (or similar material) may be laid over the DMM (201) to simulate or approximate being within a compartment of the bag (212). Those skilled in the art will appreciate that many alternative embodiments are possible that provide the disclosed benefit of encapsulating or treating the DMM (201) with the same material as the bag (212) such that light reaching the DMM (201) will be of substantially the same intensity as light reaching fluid within the fluid compartment (203).

.F DMM Temperature Sensor

The DMM (201) may, optionally, contain an internal temperature sensor. However, the physical separation of the DMM from the fluid compartment (203) means that the temperature measured this way may not strongly correlate with the fluid temperature. Nonetheless, as noted above, temperature is not a critical component of SODIS. Accordingly, the ability or inability to detect temperature is not viewed as having a significant impact on the efficacy of the preferred embodiment.

.G Bag Shape Benefits

The shape of the bag (212) (i.e. plan geometry as viewed from the front) without fluid inside of it allows it to lie flat and be stacked. This helps reduce the space necessary to ship the product in a shipping container, thereby reducing the delivered cost. That the fluid compartment (203) plan geometry is substantially a truncated rectangle rather than a square limits the maximum thickness of the filled bag in the front-to-back direction. The maximum thickness is substantially determined by the width of the fluid compartment (203) along its bottom edge. This is helpful to ensure that sunlight shining on the front reaches the back, even when the fluid is cloudy. As a trade-off, the lowest cost design to increase usable volume for a given material area would be a more circular plan, favoring a square or regular polygon with more edges.

.H DMM Orientation

The bag (212) has stiffening members—in the preferred embodiment, plastic film stiffened by addition of stiffening layers, or by virtue of welding together the layers comprising the front and back—added along its longer edges, causing the otherwise very flexible DMM compartment (202) and seam (211) joining it to the bag (212) to tend to rest at a similar orientation as the long edge of the bag (212). The preferred embodiment employs a weldable plastic film for the stiffening material (208) but other materials could be used with more involved joining requirements, such as metal, plastic, or composite struts, or specially designed fluid compartments which stiffen under fluid pressure. Thus, in some embodiments, the stiffening material could be a semi or fully rigid element.

The stiffening material (208) helps ensure that the DMM (201) remains oriented in the plane of the bag (212) when it is placed on an approximately flat surface (i.e. front of bag and front of DMM (307) are both oriented normal to the surface). The stiffening material helps prevent the DMM compartment (202) from drooping due to folding along the partitioning seam (211), mitigating the problem of the light sensor (305) facing away from the sun's path, which would otherwise result in under-estimation of the UV intensity. This solves the problem of poor sensor orientation (115) suffered by other technologies.

The perimeter of the bag may compress when the bag (212) is filled with fluid in order to accommodate the bulging (front-to-back) of the filled fluid compartment (203). This makes the perimeter welds wrinkle in a way that is difficult to predict or control, potentially deforming the DMM compartment (202) if the stiffening member was absent. If a rigid object is welded into the perimeter, e.g., near the sensor module flap, then the perimeter cannot change in this local region and this problem will not happen.

.I DMM Functional Internals

Figure 5:
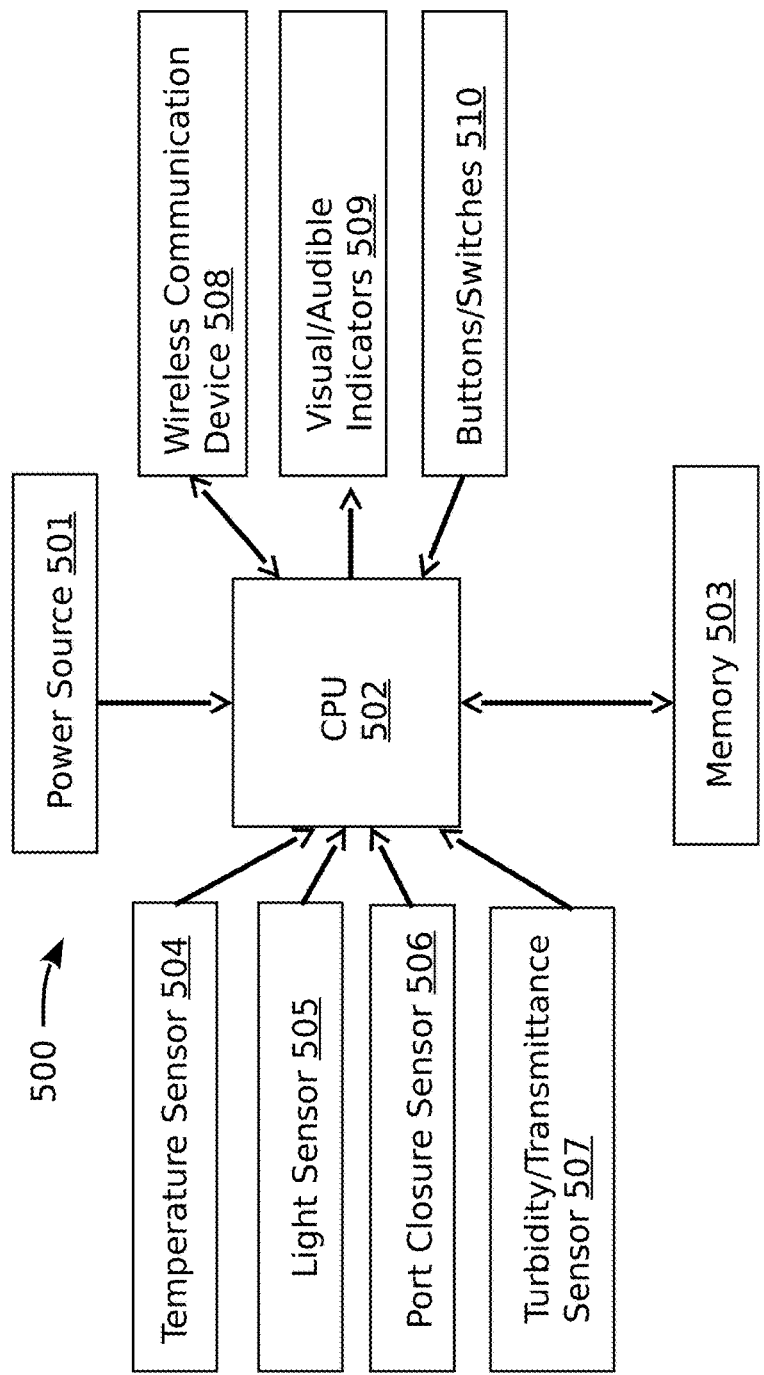
FIG. 5 is a schematic for a preferred embodiment that may be included in the disinfection system shown in FIG. 2.

FIG. 5 is a schematic view of a preferred DMM, comprising central processing unit (CPU) 502, power source 501, memory 503, sensing elements 504, 505, 506 and 507, and interface elements 508, 509 and 510. The power source 501 may include a disposable or reusable storage element (e.g. disposable battery, rechargeable battery, capacitor) as well as a generation component (e.g. photovoltaic, thermoelectric generator), or even a connection to an external power supply (e.g. AC mains power). Preferably, the power source is a coin-cell disposable battery.

The memory 503 may include volatile memory, nonvolatile memory, or both. The sensors may include a temperature sensor 504, optical sensor of radiation intensity 505 (preferably a photodiode), and either commercially-available fluid and turbidity and/or transmittance sensors 506 and 507, or specialized sensor assemblies as described in this disclosure. The interface elements include a wireless device 508 that may provide optical (e.g., infrared, or the like), acoustic, or radio frequency (RF) communication (e.g, Bluetooth, WiFi, NFC, and the like) with external systems, and in some embodiments may be a simple and low-cost element such as an antenna or an LED.

Visual/audible indicators 509, preferably "wait" (301) and "safe" (302), allow the system to communicate status information, including estimated disinfection status, to a user. The buttons/switches 510, preferably "start" (303) and "stop" (304), allow the user to initiate and control the operation of the system. In some embodiments, the indicators (509) may provide a bar chart-type representation of incremental process, including a representation of logarithmic (rather than linear) total pathogen die-off. In some embodiments the buttons/switches and indicator elements are replaced with a single element providing user input and output, such as a commercially-available LCD or similar touchscreen display. In some embodiments, status information including process (400) state and disinfection progress may be transmitted via the wireless communication device (508) instead of or in addition wireless to via the visual/audible indicators (509).

Operation of the Preferred Embodiment

To operate, the user removes the threaded fill cap (205) and fills the bag (212) with contaminated fluid, replaces the fill cap, then presses the start button (303), initiating a process substantially similar to that illustrated in FIG. 4 and described below. The process is implemented in the form of a disinfection program stored in memory (503) and executing on CPU (502) of the DMM (201). The disinfection program preferably employs an algorithm that calculates the cumulative UV light exposure and compares it to a threshold value determined via calibration. Calibration entails experimentally determining a correlation between percentage die-off of a particular representative pathogen and cumulative UV intensity measurements.

Preferably, the "wait" LED (301) blinks to indicate that the disinfection program is estimating the intensity of solar UV measured by the sensor (305) and read by the CPU (502). When the cumulative UV exposure of the bag (212) reaches a pre-determined threshold, the "wait" LED (301) stops blinking and the green "safe" LED (302) begins blinking. Preferably, if a pre-determined amount of time, such as 48 hours, elapses since the start button was pressed and the cumulative UV exposure does not reach the threshold, the system returns to a standby state (402) and stops blinking the "wait" LED (301). This is expected to occur if insufficient sunlight is available for a sustained period of time, or if the user fails to locate the system in a sunny location, which means that the SODIS process has failed. The time limit is a safe guard because the effects of the disinfection process cannot be assumed to persist with a cumulative effect if significant time periods of darkness interrupt the UV exposure; academic literature recommends a maximum of a 2-day process, allowing one night of darkness to interrupt the UV dosing period.

In an alternative embodiment, the algorithm may apply the cumulative threshold criteria to UV measurements recorded over the past e.g. 48 hours; if a threshold is exceeded, then the program transitions to the "safe" state (408); if instead a minimum threshold is not met and at least 48 hours have elapsed, the program returns to a standby state (402). This moving window approach allow successful completion of a disinfection cycle in circumstances of unreliable sunlight, e.g. in the case that after the user presses the start button, one day of low sunlight is followed by two days of half the required threshold amount each. The alternative embodiment prevents the user having to reset the process at the beginning of the second day to avoid the time limit, a decision that would require guessing the amount of UV received so far and expected on the second day.

.A Usage Tracking And Wireless Data Retrieval

The disinfection system records its own usage, preferably including the count and outcome of iterations of the disinfection process (400), of button (301, 302) presses, and of measured solar UV intensity. This information can be retrieved using a low-cost wireless communication interface (508, 306) which transmits data to a compatible receiver device, preferably a smartphone having Internet connectivity and GPS capability. The communication mode is preferably modulated infrared (IR) light, but may be visible light, using a common protocol preferably from the infrared data association (IrDA) industry standard. The DMM (201) preferably transmits data via the wireless interface (508) when either buttons (303,304) are pressed on the DMM, momentarily interrupting the normal process (400) to retrieve variables from memory (503) which are updated each time the process (400) changes state.

If visible light is used, a separate wireless emitter interface (306) may be eliminated and substituted with one of the user interface LEDs (301, 302), so that the device has no additional component cost to provide this feature. The preferably Internet-connected compatible receiver device may then record its own location (e.g., using GPS, or the like), and transmits the data and location coordinates to a database on the Internet for storage and analysis. If Internet connectivity is not available, the receiver device stores the data and transmits it to the database the next time it establishes an Internet connection.

Infrared ("IR") communication is widely used in consumer electronic products, such as remote controls for appliances, and so the electronic components mediating it are commercially available in assemblies specialized for that purpose. In this case the interface (508) is preferably an infrared (IR) LED (306). Compared to other modes of wireless communication, IR involves less engineering cost and material and component cost to design and manufacture. Other embodiments may use Wi-Fi, Satellite, cellular data, Bluetooth, ANT, or similar radio frequency (RF). In such an embodiment, the microcontroller in the device may be a Bluetooth or ANT chipset to minimize cost. In that case, the smartphone to which the data is first downloaded can be one with built-in Bluetooth or ANT capabilities.

Recording and making available for retrieval of this data is helpful because embodiments are often used as an aid item distributed free of charge to end users, and the purchasing organization is concerned with ensuring maximum and correct utilization of the product after distribution. The availability of detailed usage data is helpful feedback to enable program evaluation and iterative improvement of distribution and usage training procedures.

Some embodiments include measurement of optical properties of the fluid being disinfected. Measurement of transmittance, or "combined transmittance", are preferable to turbidity for the reasons outlined above. Measuring transmittance is beneficial because the estimate of disinfection rate can be improved by accounting for attenuation of the incident sunlight within the water. In simple terms, these embodiments measure the cloudiness of the water and model its effect on disinfection by e.g. calculating the average amount of light reaching each part of the water volume. This calculated amount will be substantially less than the incident light at the surface of the bag if the water is substantially cloudy (turbid), and knowing it allows the DMM to extend disinfection times appropriately rather than depend on a threshold rule ignoring turbidity and requiring users to avoid water greater than, for example, 30 NTU.

A measurement capturing cloudiness, including turbidity or combined transmittance value, is preferably integrated into the disinfection algorithm by scaling the estimated UV light intensity by a function of the cloudiness measurement value. This function is preferably linear, comprising a single coefficient determined by calibration experiments, but may be nonlinear.

.B Measurement Of Combined Transmittance

Figure 6:
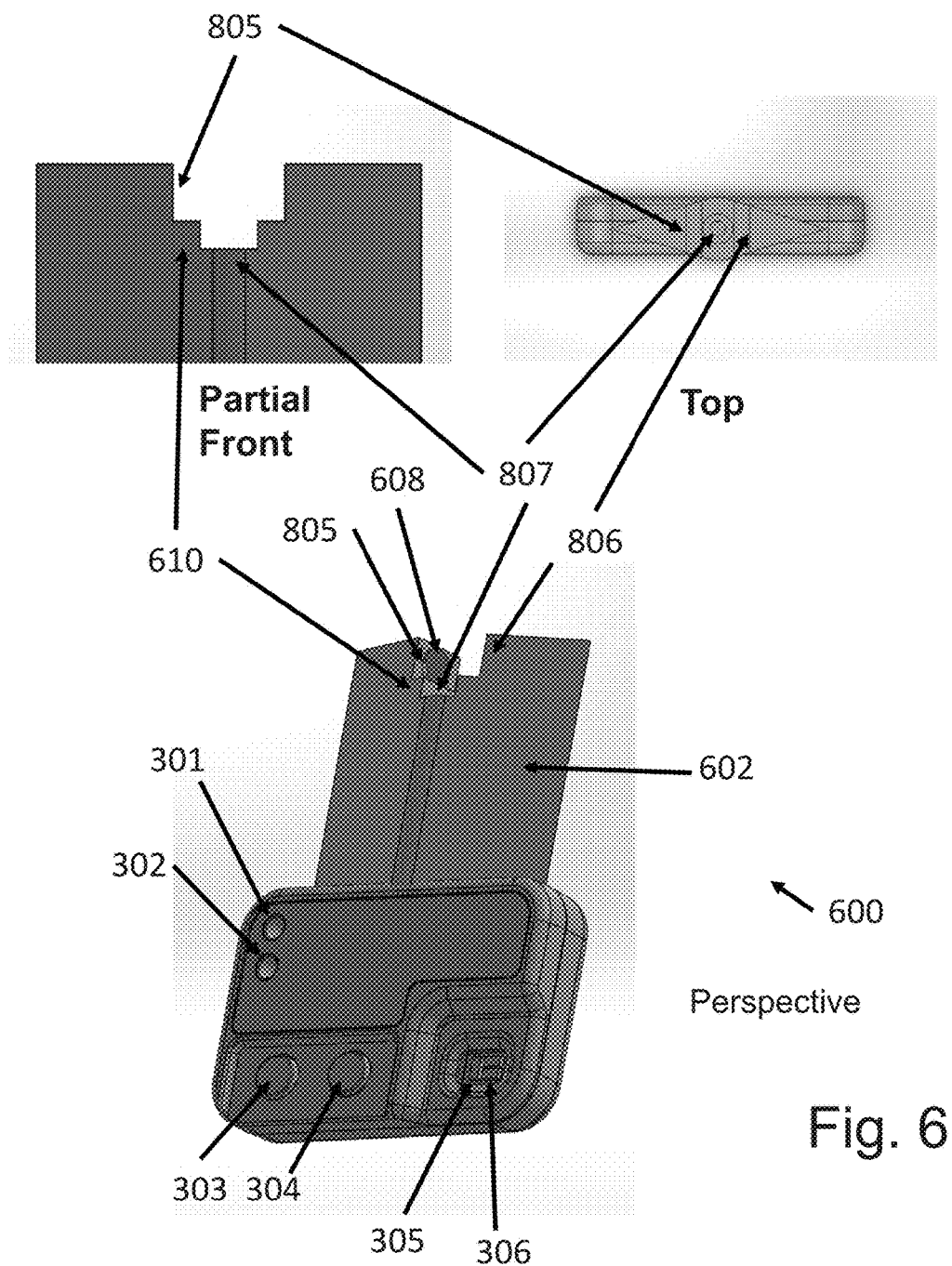
FIG. 6 is an embodiment of the DMM with a turbidity/transmittance sensor.
Figure 8:
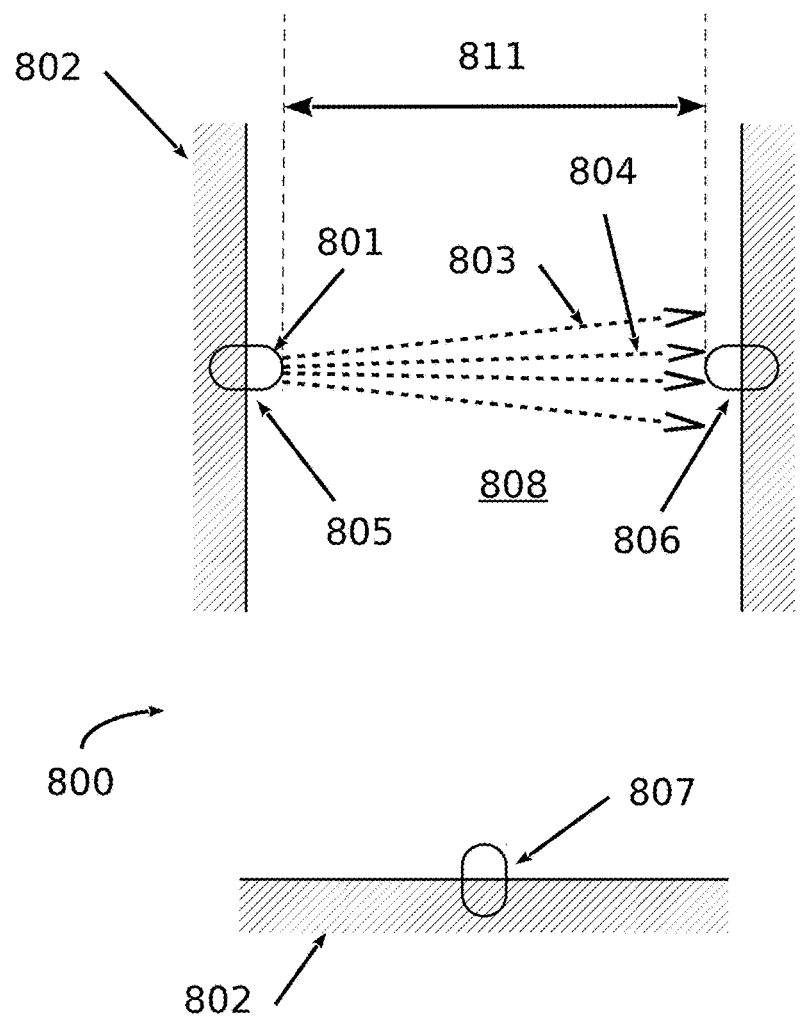
FIG. 8 is a sensor apparatus configured to measure one or more of combined transmittance, turbidity, and fluid presence.

FIG. 8 shows a schematic of an embodiment of an optical sensor apparatus that can measure a fluid's combined transmittance, or turbidity, and detect the presence of air (or any other gas with refractive index near 1.0). The optical sensor preferably may be included as a feature of the DMM shown in FIG. 6.

In one embodiment, measurement of combined transmittance is accomplished using an emitter (805) radiating light into the container's water volume (808, contiguous with 203). A direct sensor (806) is preferably situated to point directly at the emitter (805) across a short distance, oriented such that the emitted light (e.g., 803, 804) elicits a substantially maximal signal in the sensor (806). The emitter (805) is preferably a commercially-available LED packaged in an epoxy dome lens (801) and affixed to a rigid support (802), preferably the DMM protrusion (602), which ensures a specific separation distance (811) and relative orientation of emitter and sensor axes and sensors (806, 807). The sensors (806, 807) are preferably photodiodes with similar integrated lenses, and may include pre-amplifier or functionally equivalent circuits. Selective measurement of only light from the emitter, as opposed to ambient or direct sunlight, is accomplished by modulating the emitter output and measuring only changes to the modulated component of the receiver signal. A scatter sensor (807) may be oriented orthogonally to the line-of-sight between the emitter (805) and the direct sensor (806), such that it best responds to radiation scattered at a 90 degree angle to the original path of the light from the emitter (805).

The emitted light from emitter (805) follows a different radiation pattern depending on the refractive index of the fluid in the intervening space (808) following basic principles of optics. In particular, the apparatus geometry and lenses are chosen such that a change in the fluid from a lower to a higher refractive index—such as from air to water— causes increased dispersion in the radiation pattern from the emitter (805). For example, if rays of light follow one path (804) in the presence of air, they may follow a different path (803) in the presence of water, and consequently not be detected by direct sensor (806), decreasing the combined transmittance measured by the sensor apparatus. This enables the detection of fluid presence, because air will cause a higher combined transmittance measurement than can possibly be achieved with pure water. Any combined transmittance measurement lower than that of pure water is preferably attributable to cloudiness of the water, under the assumption that the fluid is either water or substantially pure air. Therefore, the single transmittance measurement from this sensor apparatus (800) can both differentiate air from water and also measure the combined transmittance.

Measuring combined transmittance over a relatively longer distance is preferred because the attenuation of light over the longer distance is greater, increasing sensitivity, and because this creates increased opportunities for scattered light from the emitter (801) to reach the sensor (806), emulating the process of solar UV arriving at locations at greater depths in the water volume via direct transmission as well as scattering.

Other embodiments of the sensor apparatus (800) may provide angles other than 90 degrees and 0 degrees between the emitter (801) and sensor (806) orientations. Still other embodiments may include only one sensor (806) but may also include multiple sensors.

.C DMM Embodiment With Sensor Apparatus

Returning to FIG. 6, shown are the physical features of one embodiment of a DMM housing (600). These physical features enable the housing to protrude into the fluid compartment (203) of the UVTC bag (212) and further to locate light emitter (805) and sensor elements (806, 807) to enable measurement of transmittance, turbidity, and detection of fluid presence via refractive index. This embodiment additionally includes mechanical features (610) to block the direct transmission of light from the emitter to the sensor oriented orthogonally to the emitter axis, in order to measure only light which is scattered onto that sensor. To reduce sensor signals caused by light other than that from the emitter (805), such as light from the sun, the housing may preferably include shrouds or counter-sinks (608) to block such interference with intended operation.

.D Temperature Sensor

DMM embodiment (600) may optionally include a temperature sensor preferably located in or at the surface of the protrusion (602) to maximize its thermal contact with the fluid compartment (203). This allows the algorithm for determining SODIS progress to optionally include water temperature.

Alternative Embodiments

.A Apparatus

Figure 7:
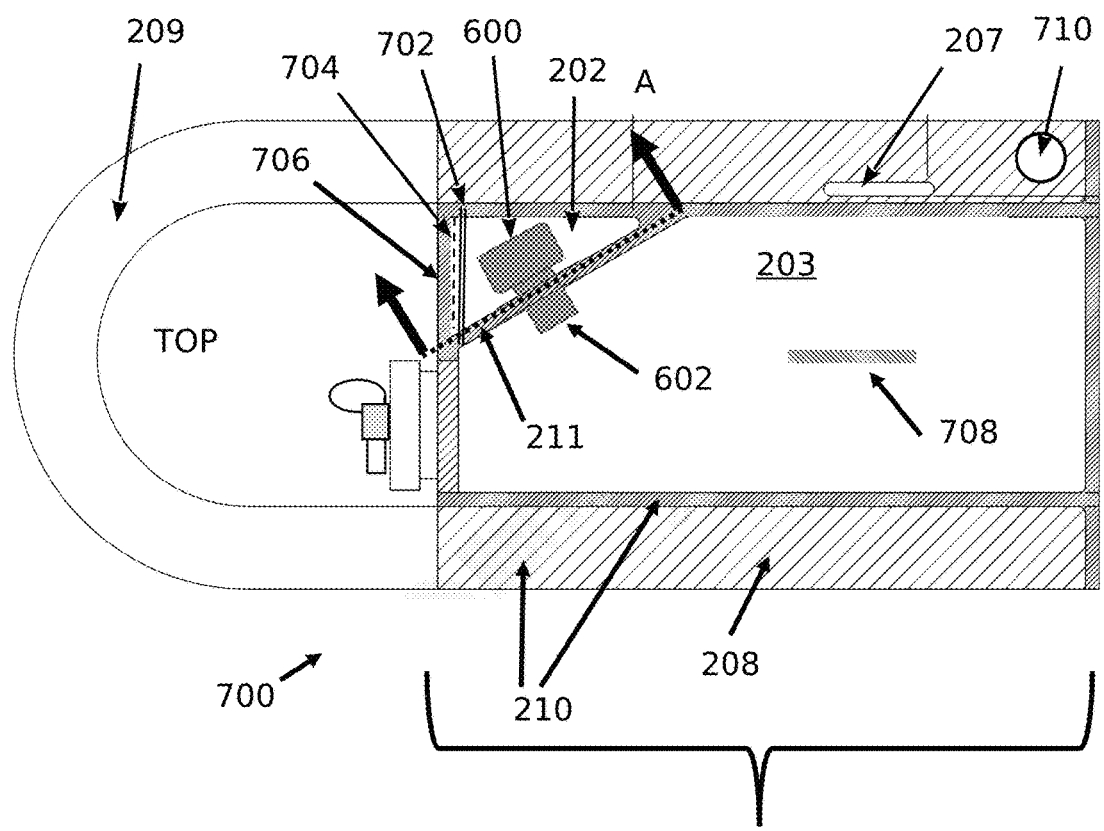
FIG. 7 is another preferred embodiment of the disinfection system.
Figure 7:
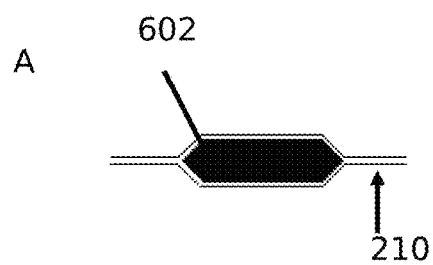

FIG. 7 shows an alternative embodiment in which the sensor apparatus (800) is included by incorporating a protrusion (602) of the DMM housing (600) from the DMM compartment (202) into the water volume within fluid compartment (203), across the partitioning welded seam (211), which locates the sensor apparatus (800) within the water volume of the fluid compartment (203).

Also shown in FIG. 7 are additional aspects of alternative embodiments. Access to the DMM (600) for maintenance, replacement, or battery replacement, may be provided by an opening in the monitor compartment (202), such as a low-cost re-sealable zipper closure (702) which is further secured by a welded seam (706), such that cutting along a specific path (704) bypasses the seam (706) and grants access to the compartment (202) via the re-sealable closure (702).

One or more baffles (708) in the bag (212), comprising a weld within the fluid compartment (203) or a piece of film welded between the front and rear bag surfaces with the same weld plan, allow the bag (212) to have a greater internal volume if its dimensions are increased, while still limiting the maximum front-to-rear thickness of the filled bag. One or more grommets (710) or similar reinforced openings in the stiffening material (208) or welded seams (210) allow embodiments to be hung, such as on a nail, post, or rope for conveniently dispensing water.

.B Process

Figure 4:
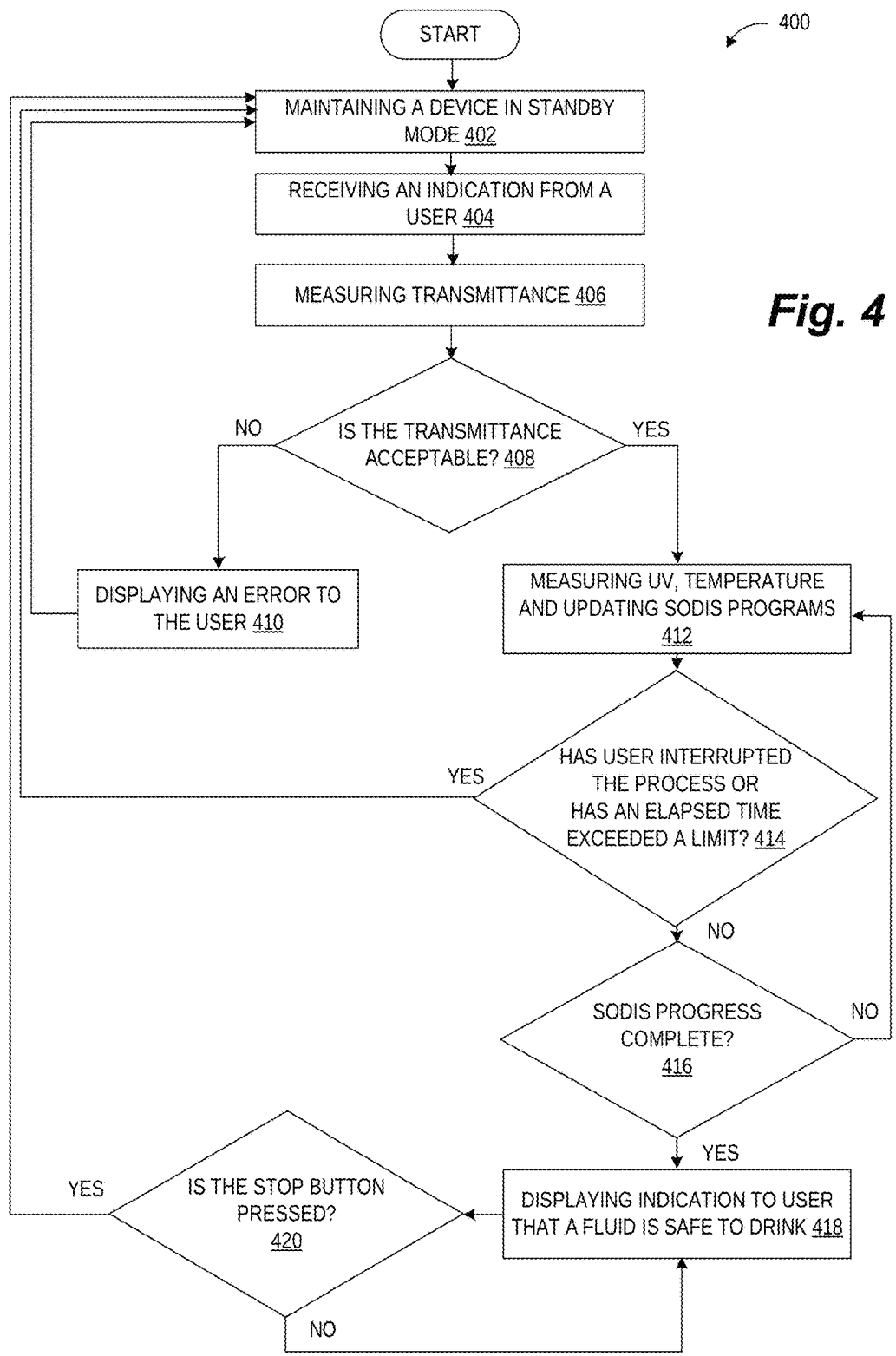
FIG. 4 is a preferred process for disinfecting a fluid using the disclosed embodiments.

FIG. 4 is an illustrative process (method 400) for performing solar disinfection in accordance with the preferred embodiment. At 402, method 400 includes maintaining a device in standby mode. At 404, method 400 includes receiving an indication from a user. The user preferably may depress the "start" button (303) as an indication to prompt method (400) to advance to the next step, preferably SODIS update (412), skipping states (406, 408). However in some embodiments, the process may start by advancing to measuring transmittance. In still other embodiments, the method 400 may start by automatically advancing from standby (402) to measuring transmittance (406). Some embodiments advance to SODIS (412) only if the transmittance is within a prescribed range, precluding operation if it is too low (insufficient UV reaching the water) or too high (indicative of air rather than water between the emitter (805) and sensor (806)).

At 406, method 400 includes measuring transmittance of a fluid, but in some embodiments this includes measurement of combined transmittance and/or turbidity. At 408, method 400 determines if the transmittance is acceptable. If it is not, at 410 method 400 includes displaying an error to the user and returns the device to standby mode at 402. If it is, the system begins estimation of the SODIS process at 412 by measuring one or more of UV, temperature, and updating SODIS programs.

The SODIS process may estimate other environmental and fluid conditions before execution of methods for estimating a disinfection status. At 414, method 400 includes determining if a disinfection status calculation has been interrupted. For example, the disinfection status calculation may be interrupted by the user pushing the stop button (304). Further, the disinfection status calculation may be interrupted by environmental, fluid, and/or time conditions if such conditions fall outside a specified range, including combined transmittance. If an interruption or unacceptable condition occurs at 414, method 400 returns to the standby state at 402. If NO, method 400 includes determining if the SODIS is complete at 416. If YES, at 418 method 400 includes displaying an indication to the user that the fluid is safe to drink.

In this way, the system transitions from a calculative state to a safe state in which it indicates to the user that the fluid is disinfected, preferably by blinking the "safe" indicator 302. At 420, method 400 includes determining if the user provides a command, preferably pressing the "stop" button 304. If NO, method 400 includes continuing to display that the fluid is safe to drink. If YES, method 400 may restart and trigger a return to standby at 402. It should be appreciated that method 400 is provided as an example and may include additional steps. Further, method 400 may be completed by omitting one or more steps. Further still, it shall be appreciated that the particular order of method 400 as shown in FIG. 4 may be configured in another order in other embodiments. This process flow represents a simplified description of one embodiment only.

.C Detection Of Container Opening

To prevent accidental or intentional incorrect use of the device (e.g. changing the water in the unit without resetting, creating the appearance of treated water) in some embodiments, a sensor (406) detects whether the screw cap (205) or equivalent inflow/outflow port is opened. The sensor may be a simple mechanical switch depressed by the screw cap (205) moving into closed position. In the process (400), the port sensor detecting a closed state replaces indication from a user (404), and detection of an open state replaces stop (420) and user-triggered interruption (414). In other embodiments, the process (400) can refuse to enter the in-progress state (412) until the port is in a closed state.

.D Auto-Start

Some embodiments have a different method of initiating and stopping process (400). Rather than require a user to press the start and stop buttons, implicitly informing the disinfection monitor of when untreated water is present in the bag, these alternative embodiments automatically begin the disinfection process when water is detected by the combined transmittance sensor, and automatically return to the standby state when air is detected. This is implemented in process 400 by skipping state 404 and using high transmittance (indicating air detection) as an interruption condition in state 414. If air is detected for only a short time duration, the process may preferably continue, allowing the possibility that an air bubble came in contact with the combined transmittance sensor.

These embodiments address the problem that the user is depended upon to tell the system when to start the disinfection process, and may intentionally or unintentionally replace treated water with untreated water whilst the disinfection monitor continues to indicate "safe" status.

A variation on the automatically starting and stopping embodiments is to preserve at least a button-triggered stop condition (420) to return to standby (402) so that the user can reduce the power used by the system when "safe" indication (418) is no longer necessary, and also enjoy greater manual control over the system's operation.

The welded seam 211 is included as a consequence of the cut-and-weld manufacturing process and may be substituted with elements similarly providing structural reinforcement, attachment of different materials, and partitioning of compartments, in other embodiments. The threaded port 204 and spigot 206 may be substituted with other elements providing a re-closeable fill and dispensing port, including separation of the fill port and dispense port, in other embodiments.

Specific Implementation of Preferred Embodiment

FIG. 9 includes photographs of one embodiment in which the DMM (201) measures only UV intensity, and the UVTC is a bag with reinforcing material (208) affixed along the long edges of the bag and continuing in a loop to form a strap (209) for carrying the system. The DMM (201) is also shown in a separate photo, removed from its compartment (202).

CONCLUSION

It will be appreciated that the configurations and routines disclosed herein are exemplary in nature, and that these specific embodiments are not to be considered in a limiting sense, because numerous variations are possible. For example, the above technology can be applied to other types of fluids; thus, it is to be appreciated that the technology is not limited to the disinfection of water. Further, the above technology can be applied to other sources of UV light and is not limited to UV light from the sun. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

Other embodiments may include combinations and sub-combinations of features described above or shown in the several figures, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, "feature" or "features" can refer to structures and/or functions of an apparatus, article of manufacture or system, and/or the steps, acts, or modalities of a method.

In the foregoing description, numerous details have been set forth in order to provide a sufficient understanding of the described embodiments. In other instances, well-known features have been omitted or simplified to not unnecessarily obscure the description. A person skilled in the art in view of this description will be able to practice the disclosed invention. The specific embodiments disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

What is claimed is:

1. A device to measure photodisinfection treatment of water by ultraviolet radiation from the sun, comprising:

a container for holding the water, the container being substantially transparent to the radiation, the container being further configured to enhance exposure of the water to the radiation by a geometric design that limits the cross-section of the water volume in a primary direction of incident radiation, the container comprising two or more laminates, wherein at least one laminate is substantially transparent to UV-A radiation, or UV-B radiation, or both UV-A and UV-B radiation, and at least one other laminate is not transparent to either UV-A radiation or UV-B radiation but provides structural robustness to the container, and further wherein at least one laminate is reflective such that incident UV radiation passing through the container is reflected back into the container, thereby increasing the rate of treatment;

an optical sensing component configured to estimate an intensity of radiation incident to a face of the optical sensing component and having wavelengths that correlate with the treatment, the optical sensing component being affixed to the container such that the face of the optical sensing component is oriented normal to a primary path of the radiation, the optical sensing component being disposed within the container so that the radiation incident upon the optical sensing component passes through the same material as the radiation incident upon the water; and a computing component that estimates treatment progress using optical sensor measurements over time, allows a user to initiate or terminate treatment process monitoring, and provides an indication of treatment progress.

2. A device to measure photodisinfection treatment of water by ultraviolet radiation from the sun, comprising:
  a container for holding the water, the container being substantially transparent to the radiation, the container being further configured to enhance exposure of the water to the radiation by a geometric design that limits the cross-section of the water volume in a primary direction of incident radiation;
  an optical sensing component configured to estimate an intensity of radiation incident to a face of the optical sensing component and having wavelengths that correlate with the treatment, the optical sensing component being affixed to the container such that the face of the optical sensing component is oriented normal to a primary path of the radiation, the optical sensing component being disposed within the container so that the radiation incident upon the optical sensing component passes through the same material as the radiation incident upon the water; and
  a computing component that estimates treatment progress using optical sensor measurements over time, allows a user to initiate or terminate treatment process monitoring, and provides an indication of treatment progress.

3. A device to measure photodisinfection treatment of water by ultraviolet radiation from the sun, comprising:
  a container for holding the water, the container being substantially transparent to the radiation, the container being further configured to enhance exposure of the water to the radiation by a geometric design that limits the cross-section of the water volume in a primary direction of incident radiation;
  an optical sensing component configured to estimate an intensity of radiation incident to a face of the optical sensing component and having wavelengths that correlate with the treatment, the optical sensing component being affixed to the container such that the face of the optical sensing component is oriented normal to a primary path of the radiation; and
  a computing component that estimates treatment progress using optical sensor measurements over time, allows a user to initiate or terminate treatment process monitoring, and provides an indication of treatment progress.

4. A device to measure photochemical treatment of a fluid by radiation from an external source, comprising:
  a container for holding the fluid, the container being substantially transparent to the radiation, the container being further configured to enhance exposure of the fluid to the radiation by a geometric design that limits the cross-section of the fluid volume in a primary direction of incident radiation;
  an optical sensing component configured to estimate an intensity of radiation incident to a face of the optical sensing component and having wavelengths that correlate with the treatment, the optical sensing component being affixed to the container such that the face of the optical sensing component is oriented normal to a primary path of the radiation; and
  a computing component that estimates treatment progress using optical sensor measurements over time, allows a user to initiate or terminate treatment process monitoring, and provides an indication of treatment progress.

5. The device recited in claim 4, wherein the photochemical treatment of the fluid comprises photodisinfection of water.

6. The device recited in claim 4, wherein the external source of radiation comprises ultraviolet radiation from the sun.

7. The device recited in claim 4, wherein maximizing exposure to radiation is accomplished by the inclusion of reflective surfaces.

8. The device recited in claim 4, wherein the treatment progress comprises a binary indication of completeness with respect to a particular threshold criteria.

9. The device recited in claim 4, wherein the optical sensing component is disposed within the container so that the radiation incident upon the optical sensing component passes through the same material as the radiation incident upon the fluid, or through material having substantially the same optical properties as the container.

10. The device recited in claim 4, further comprising a temperature sensing component configured to detect a temperature of the fluid, and wherein the computing component is further configured to include the temperature in the estimation of treatment progress.

11. The device recited in claim 4, wherein the optical sensing component and the computing component are further configured to measure one or more of turbidity and transmittance of the fluid.

12. The device recited in claim 4, wherein the container is a flexible structure constructed of laminates of plastics.

13. The device recited in claim 12, wherein the container is a bag comprised of two or more laminates, wherein one laminate is substantially transparent to UV-A and UV-B radiation, and the other laminate is not necessarily transparent to UV-A or UV-B but provides structural robustness to the container.

14. The device recited in claim 4, wherein the other laminate is reflective such that incident UV radiation passing through the container is reflected back into the container, thereby increasing the rate of treatment.

15. The device recited in claim 4, wherein the other laminate is absorptive black, such that incident radiation is converted to heat, thereby raising the temperature of the fluid.

16. The device recited in claim 4, wherein the computing component automatically starts measuring treatment progress when the container is secured shut, and automatically resets treatment progress when the container is opened.

17. The device recited in claim 4, further comprising a 'Start' button that initiates treatment measurement, an 'Off/Reset' button to restart treatment measurement, and one or more visual indicators of treatment process status.

18. A device to measure photochemical treatment of a fluid by radiation from an external source, comprising:
  a container having a first compartment for holding the fluid, the container being substantially transparent to the radiation, the container being further configured to enhance exposure of the fluid to the radiation by a geometric design that limits the cross-section of the fluid volume in a primary direction of incident radiation, the container having a second compartment;
  an optical sensing component disposed within the second compartment of the container, the optical sensing component being configured to estimate an intensity of radiation incident to a face of the optical sensing component and having wavelengths that correlate with the treatment, the optical sensing component being affixed to the container such that the face of the optical sensing component is oriented normal to a primary path of the radiation;

a computing component that estimates treatment progress using optical sensor measurements over time, allows a user to initiate or terminate treatment process monitoring, provides an indication of treatment progress, and stores data representative of usage of the device over time; and a wireless communication component configured to transmit the stored data to a remote computing device.

19. The device recited in claim 18, wherein the wireless communication component is further configured to interact with the remote computing device over a local area wireless communication protocol.

* * * * *